(12) United States Patent
Potisek et al.

(10) Patent No.: US 9,505,731 B2
(45) Date of Patent: *Nov. 29, 2016

(54) EPOXIDE COMPOUND

(71) Applicant: Dow Global Technologies LLC, Midland, MI (US)

(72) Inventors: Stephanie L. Potisek, Houston, TX (US); Robert J. Wright, Sugar Land, TX (US); Michael J. Mullins, Houston, TX (US)

(73) Assignee: BLUE CUBE IP LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/423,741

(22) PCT Filed: Oct. 25, 2013

(86) PCT No.: PCT/US2013/066737
§ 371 (c)(1),
(2) Date: Feb. 25, 2015

(87) PCT Pub. No.: WO2014/066717
PCT Pub. Date: May 1, 2014

(65) Prior Publication Data
US 2015/0225359 A1    Aug. 13, 2015

Related U.S. Application Data

(60) Provisional application No. 61/718,752, filed on Oct. 26, 2012.

(51) Int. Cl.
| | | |
|---|---|---|
| C07D 303/04 | (2006.01) | |
| C07D 301/03 | (2006.01) | |
| C08G 59/24 | (2006.01) | |
| C07C 2/76 | (2006.01) | |
| C07D 301/12 | (2006.01) | |
| C07D 301/14 | (2006.01) | |
| C07D 301/19 | (2006.01) | |
| C09D 5/28 | (2006.01) | |
| C09D 175/04 | (2006.01) | |
| C08G 59/32 | (2006.01) | |

(52) U.S. Cl.
CPC .............. *C07D 303/04* (2013.01); *C07C 2/76* (2013.01); *C07D 301/03* (2013.01); *C07D 301/12* (2013.01); *C07D 301/14* (2013.01); *C07D 301/19* (2013.01); *C08G 59/24* (2013.01); *C09D 5/28* (2013.01); *C09D 175/04* (2013.01); *C07C 2531/24* (2013.01); *C08G 59/32* (2013.01)

(58) Field of Classification Search
CPC C07D 303/04; C07D 301/03; C07D 301/12; C07D 301/14; C07D 301/19; C07C 2/76; C08G 59/24

USPC ........................................................ 549/512
See application file for complete search history.

(56) References Cited

U.S. PATENT DOCUMENTS

| | | | |
|---|---|---|---|
| 3,053,856 A | 9/1962 | Deming et al. | |
| 3,476,693 A * | 11/1969 | Mango ................. | C07D 303/04 156/330 |
| 5,264,606 A | 11/1993 | Moloy et al. | |
| 2015/0225359 A1* | 8/2015 | Potisek ................ | C07D 301/03 549/512 |

FOREIGN PATENT DOCUMENTS

| | | |
|---|---|---|
| DE | 1160850 B | 1/1964 |
| GB | 1185137 A | 3/1970 |
| JP | 2011195483 A | 10/2011 |
| WO | WO 2010077483 A1 | 7/2010 |
| WO | WO 2011114935 A | 9/2011 |
| WO | WO 2012020661 A1 | 2/2012 |
| WO | WO 2014066717 A1 | 5/2014 |

OTHER PUBLICATIONS

Lane et al., Metal-Catalyzed Epoxidations of Alkenes with Hydrogen Peroxide, K. Chem. Rev., 2002, 103(7), pp. 2457-2473.
Sharpless et al., On the Mechanism of Titanium-Tartrate Catalyzed Asymmetric Epoxidation, Pure & Appl. Chem., 1983, vol. 55(11), p. 1823-1836.
Crivello and Dietliker, Chemistry & Technology of UV & EB Formulation for Coatings, Inks & Paints, vol. 3, 1991, p. 329.
Lee, H. and Neville, K., Handbook of Epoxy Resins, McGraw-Hill Book Company, New York, 1967, Chapter 2, pp. 2-1 to 2-27.
Eyrisch, et al., Ethenolysis of Functionalized Cycloolefins, Designed Monomers and Polymers (2004), vol. 7(6), pp. 661-676.
European Patent Office, Written Opinion of the International Searching Authority dated Apr. 26, 2015 for PCT/US2013/066737.
European Patent Office, International Search Report dated Jan. 5, 2014 for PCT/US2013/066737.
European Patent Office, International Preliminary Report on Patentability dated Apr. 28, 2015 for PCT/US2013/066737.

* cited by examiner

*Primary Examiner* — T. Victor Oh
(74) *Attorney, Agent, or Firm* — Polsinelli PC

(57) ABSTRACT

A novel low viscosity epoxide having the following general Structure (I): Structure (I) wherein R1 and R2 can be, but is not limited to, hydrogen or a hydrocarbon group having from C1 to about C20 carbon atoms; with the proviso that R1 and R2 are not both hydrogen.

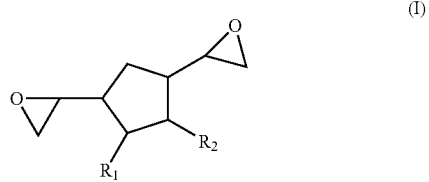

(I)

21 Claims, No Drawings

EPOXIDE COMPOUND

FIELD

The present invention is related to a novel epoxy compound.

BACKGROUND

With the development of many epoxy industries, there are increasing material demands, and new epoxy compounds that can provide better material properties are needed. For example, epoxies that can provide thermosets with high glass transition temperatures are needed for the aerospace industry; epoxies that have low viscosities are needed for the semiconductor packaging industry; and epoxies that have enhanced UV stability are needed in the coatings industry.

SUMMARY

In one embodiment, the present invention is directed to a novel epoxide compound; and in another embodiment, the present invention is directed to a process for producing the novel epoxide compound.

One general embodiment of the present invention includes an epoxide compound illustrated by the following general Structure (I):

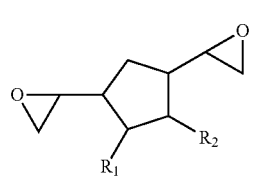

Structure (I)

wherein $R_1$ and $R_2$ comprises hydrogen or a hydrocarbon group having from C1 to about C20 carbon atoms; with the proviso that $R_1$ and $R_2$ are not both hydrogen.

In another embodiment, $R_1$ and $R_2$ can each individually be, but are not limited to, for example a hydrocarbon group having from C1 to about C20 carbon atoms including for example aliphatic, cycloaliphatic, and bicyclic groups. $R_1$ and $R_2$ can also be joined to form a cycloaliphatic or bicycloaliphatic ring. In another embodiment, the C1 to C20 carbon atoms of $R_1$ and $R_2$ may contain an oxirane ring attached to any one of the carbon atoms of the $R_1$ and/or $R_2$ groups.

One preferred embodiment of the composition of matter of the present invention included in the above Structure (I) and described herein may include divinylhexahydropentalene triepoxide (DVHPTO) having the following chemical Structure (II):

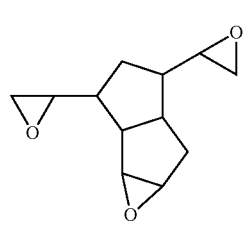

Structure (II)

Another embodiment of the composition of matter of the present invention included in the above Structure (I) and described herein may include a compound having the following chemical Structure (III):

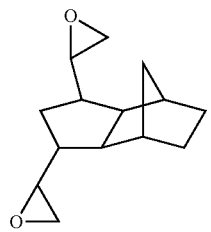

Structure (III)

Another embodiment of the composition of matter of the present invention included in the above Structure (I) and described herein may include a compound having the following chemical Structure (IV):

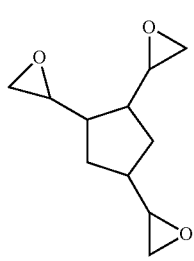

Structure (IV)

Another general embodiment of the present invention is directed to a process for preparing the novel epoxide compounds represented by Structures (I)-(IV) including the steps of: (a) ring-opening metathesis of a cyclic olefin, and (b) epoxidizing the product of step (a) with at least one oxidizing agent.

DESCRIPTION

"Hydrocarbon" herein means a group that contains at least one carbon atom and may include an oxygen atom or other heteroatoms.

One broad scope of the present invention includes a compound having the following Structure (I):

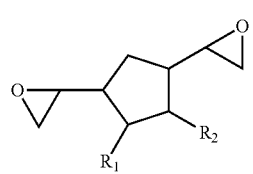

Structure (I)

wherein $R_1$ and $R_2$ comprises hydrogen or a hydrocarbon group having from C1 to about C20 carbon atoms; with the proviso that $R_1$ and $R_2$ are not both hydrogen.

For example, in one embodiment, the compound of the present invention may have the structure as shown in Structure (II) as follows:

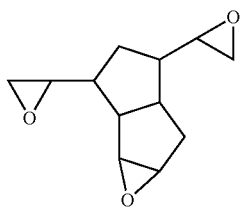

Structure (II)

For example, in another embodiment, the compound of the present invention may have the structure as shown in Structure (III) as follows:

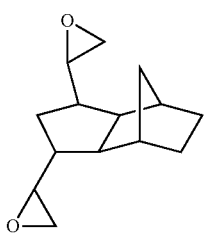

Structure (III)

For example, in another embodiment, the compound of the present invention may have the structure as shown in Structure (IV) as follows:

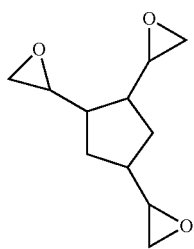

Structure (IV)

Another broad embodiment of the present invention includes a process for preparing the novel epoxide compound above including for example reacting or epoxidizing a cyclic olefin reactant with at least one oxidizing agent to form the above compound of Structure (I).

The process of preparing the novel epoxide compound of the present invention having Structure (I) above includes, for example, epoxidizing an olefin reactant with at least one oxidizing agent. Generally, the oxidizing agent or oxidant is used in the range from about 0.1 to about 100 equivalents per alkene in one embodiment, from about 0.5 to about 20 equivalents per alkene in another embodiment, and from about 1 to about 3 equivalents per alkene in still another embodiment.

The epoxidation process may be carried out at a predetermined temperature and for a predetermined period of time sufficient to form the novel epoxide compound. For example, the temperature of the epoxidation step may be generally from about −20° C. to about 200° C. in one embodiment; from about −10° C. to about 150° C. in another embodiment; from about −5° C. to about 100° C. in still another embodiment, and from about 0° C. to about 80° C. in yet another embodiment.

The pH of the reaction mixture depends on the oxidation chemistry used to prepare the epoxide compound of the present invention. In general, the pH of the reaction mixture is maintained at a pH of from about 5 to about 11 in one embodiment.

The epoxidation reaction process time may be chosen between about 10 minutes to about 24 hours in one embodiment, and between about 1 hour to about 5 hours in another embodiment. Below a period of time of about 10 minutes, the time may be too short to ensure sufficient epoxidation of the alkene reactant; and above about 24 hours, the time may be too long to be practical or economical.

In one preferred embodiment, for example, the process of preparing the novel epoxide compound of the present invention above includes reacting a cyclic olefin such as 1,3-divinyl-1,2,3,3a,4,6a-hexahydropentalene (DVHP) also referred to as 2,4-divinylbicyclo[3.3.0]oct-6-ene with at least one oxidizing agent under reaction conditions to form an epoxide compound having the above general chemical structure as illustrated by Structure (II) above.

In another embodiment, the process for preparing DVHPTO may include for example a two-step process, wherein as a first step, providing a precursor DVHP and then as a second step, epoxidizing the DVHP with an oxidizing agent under process reaction conditions to generate DVHPTO.

In one preferred embodiment, the precursor DVHP used in the first step of the above two-step process may be synthesized by any synthesis process known in the art such as for example by a ring-opening metathesis process or ethenolysis of dicyclopentadiene (DCPD) as described for example in U.S. Pat. No. 5,264,606, incorporated herein by reference.

The first step of preparing the precursor DVHP described above can be shown in the first step of the following two-step reaction scheme:

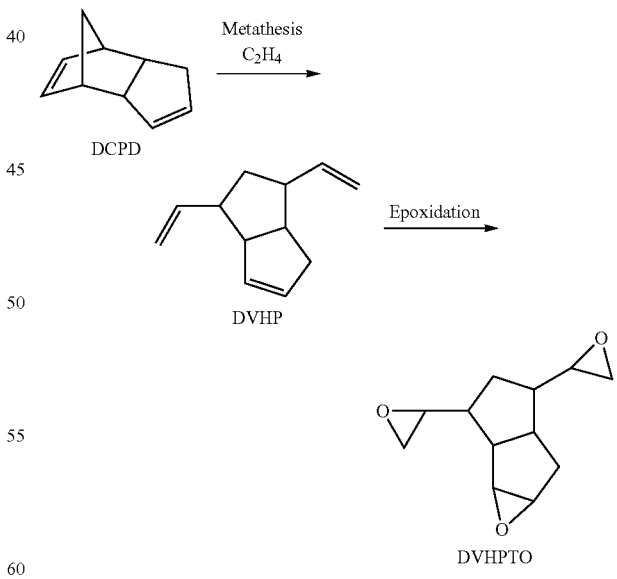

The first step of the above scheme, a ring-opening metathesis process, is used to prepare the precursor DVHP. In the above scheme, the formation of DVHP is then followed by epoxidation of the DVHP.

The epoxidation second step illustrated in the above scheme can be carried out using various epoxidation processes. For example, one useful process can include reacting DVHP with an oxidant to form the DVHPTO epoxide compound of the present invention. In one preferred embodiment, the oxidant or oxidizing agent used in the above epoxidation second step of the above two-step process may include for example oxidizing agents such as percarboxylic acids such as peracetic acid or meta-chloroperoxybenzoic acid.

Alternatively, the epoxidation reaction second step can be carried out using peroxomonosulfates such as Oxone® with acetone to form epoxides from the DVHP. (Oxone is a trademark of E.I. du Pont de Nemours and Company.)

In another embodiment, non-metal catalyzed reactions with hydrogen peroxide ($H_2O_2$) can also be used as the epoxidizing agent for DVHP in the second step; as described for example, in U.S. Pat. No. 3,053,856 which uses hydrogen peroxide and acetonitrile to form a peroxyimidic acid that acts as the epoxidizing agent.

In still another embodiment, metal-catalyzed epoxidations with hydrogen peroxide as described in Lane et al., *K. Chem. Rev.,* 2002, 103(7), pp. 2457-2473 can be used in the epoxidation reaction step of DVHP to form the epoxide of the present invention. Some examples of reactions discussed in the above Lane et al. reference include reactions using an Fe(III) complex of pyridine 2,6-dicarboxylic acid, Mn(III) complexes of 8-hydroxyquinoline and halogen substituted analogs, and Mn(III) salen complexes. Other epoxidizing agents outlined in this class include metal organic compounds such as methyltrioxo rhenium.

In yet another embodiment, transition metal catalysts can be combined with alkylhydroperoxides to perform the epoxidation of the DVHP. An example of this type of chemistry includes the epoxidation reaction which utilizes a titanium catalyst, chiral tartrate diester, and tert-butylhydroperoxide as described in Sharpless et al., *Pure Appl. Chem.,* 1983, 55, p. 1823.

In yet one other embodiment, in the second epoxidation step, heteropoly acid salts with phase transfer ammonium cations, zeolites and hydrotalcites, and metal oxides can also be used as the epoxidizing reagents.

DVHPTO is a novel compound; and generation of DVHPTO in high yield may be confirmed by instrumentation and equipment such as gas chromatography/mass spectrometry (GC-MS) and $^1H$ and $^{13}C$ NMR spectroscopy. The GC trace shows that only one major product is formed (composed of different stereoisomers), while the mass spectrometry data confirms that it has the expected m/z of 208.1 for DVHPTO. Analysis by $^1H$ and $^{13}C$ NMR spectroscopy reveals a complicated set of resonances because of the different stereoisomers generated upon epoxidation of DVHP.

Additional components in addition to the triepoxide may be found in the DVHPTO product, including the mono- and di-epoxides. Length of the reaction and amount of oxidant may affect the product distribution.

The various novel epoxy compounds described with reference to Structure (I), advantageously can have one or more beneficial properties including for example low viscosity, absence of chlorine atoms, low volatility, and when cured, a thermoset with high glass transition temperatures (Tg).

In one illustrative embodiment of the present invention, when the novel epoxy compound is, for example DVHPTO, the DVHPTO exhibits several beneficial properties including for example a low viscosity which is advantageously used in preparing a curable liquid formulation for further processing. DVHPTO comprises a low viscosity liquid epoxy compound which, for example, generally has a viscosity of less than about 0.3 Pa s in one embodiment; from about 1.0 Pa s to about 0.001 Pa s in another embodiment, from about 0.5 Pa s to about 0.01 Pa s in still another embodiment, and from about 0.3 Pa s to about 0.02 Pa s in yet another embodiment, at 25° C. The viscosity of DVHPTO is much lower than standard liquid epoxy resins known in the art which typically are 10 Pa s or higher.

In one embodiment, DVHPTO may exhibit low vapor pressure generally in the range of from about 0.001 mmHg to about 0.0000001 mmHg at 25° C., and from about 0.0001 mmHg to about 0.0000001 mmHg, in another embodiment.

In one embodiment, DVHPTO may comprise a "clean resin", that is, a resin that does not contain halogens such as chlorine. For example, the DVHPTO prepared by the process of the present invention contains less than about 500 ppm total chlorine in on embodiment, less than 100 ppm total chlorine in another embodiment, and less than about 50 ppm total chlorine in still another embodiment. The present invention process provides a DVHPTO compound with low levels of chlorine because the DVHPTO can be prepared from a starting material other than epichlorohydrin. In general, DVHPTO contains 0 ppm to less than about 500 ppm of halogens in one embodiment, from about 1 ppb to about 500 ppm in another embodiment, and from about 1 ppb to about 200 ppm in still another embodiment.

In one preferred embodiment, DVHPTO is a cycloaliphatic compound that does not contain any aromatic functionality. The material lacking an aromatic functionality means the material is stable in the presence of UV light.

The DVHPTO compound of the present invention may be used to make curable formulations or compositions which, in turn, can be cured to form thermosets exhibiting improved or a balance of properties.

One embodiment of the present invention is directed to providing a curable resin formulation or composition that can be thermally cured or UV cured comprising the novel liquid epoxide compound of the present invention. For example, in one embodiment, the curable composition of the present invention that can be thermally cured can include (a) at least one novel liquid epoxide compound of the present invention such as DVHPTO; and (b) at least one curing agent such as an amine, an anhydride, a phenolic curing agent or mixtures thereof. One of the advantages of using the novel compound of the present invention in a curable composition using a curing agent is the flexibility to use a variety of curing agents, such as amines, that have not typically been capable of being used with a curable composition containing known cycloaliphatic epoxy resins. As known in the art, a cycloaliphatic epoxy is derived from oxidation of a cycloolefin. Other optional additives known to the skilled artisan can be included in the curable composition such as for example a curing catalyst.

In addition to the epoxide useful in preparing the curable composition such as the novel liquid DVHPTO epoxy compound described above, the thermally curable composition of the present invention may comprise, for example, a curing agent. In general, the curing agent blended with the novel compound of the present invention to prepare the curable composition may comprise, for example, any conventional curing agent known in the art useful for including in a curable composition. The curing agent, (also referred to as a hardener or cross-linking agent) useful in the curable composition, may be selected, for example, but are not limited to, anhydrides, carboxylic acids, amine compounds, phenolic compounds, mercaptans, or mixtures thereof.

Examples of curing agents useful in the present invention may include any of the co-reactive or curing materials known to be useful for curing epoxy resin based compositions. Such co-reactive curing agents include, for example, amines, polyamines, polyamides, polyaminoamides, dicyandiamide, mercaptans, polycarboxylic acids and anhydrides, and any combination thereof or the like. Other specific examples of co-reactive curing agents include styrene-maleic acid anhydride (SMA) copolymers, amine co-reactive curing agents including diaminodiphenylsulfone, methylene dianiline, aminoethanol, propylene diamine, diethylene triamine, triethylene tetramine, tetraethylene pentamine, aminated polyols such as Jeffamines (Huntsman trademark), cycloaliphatic amines such as isophorone diamine, bis-paraaminocyclohexyl methane, and 1,2-diaminocyclohexane, piperidine, aminoethyl pidperidine, "Mannich bases" derived from condensations of resoles with alkylene polyamines such as ethylene diamine and xylylene diamine; and mixtures thereof.

Specific examples of phenolic curing agents useful in the present invention include bisphenols of the formula $HOC_6H_4$—Z—$C_6H_4OH$ where Z is 2,2-propylidene, 1,1-ethylidene, 1,2-ethylidene, methylene, sulfone, and oxygen, phenolphthalein; and mixtures thereof. Other specific examples include polyphenols (novolacs) such as condensation products of phenols with aldehydes.

Specific examples of anhydride curing agents useful in the present invention include maleated hydrocarbon polymers such as maleated polybutadiene, copolymers of maleic anhydride with styrene, polyphthalic anhydrides, cycloaliphatic anhydrides such as nadic anhydride, methyl nadic anhydride, methyl hexahydrophthalic anhydride; and mixtures thereof.

Among the conventional co-reactive epoxy curing agents, amines and amino or amido containing resins, anhydrides, and phenolics are preferred.

Generally, the amount of the curing agent used in the curable composition of the present invention, may be for example, from about 5 wt % to about 95 wt % in one embodiment, from about 10 wt % to about 90 wt % in another embodiment; from about 15 wt % to about 95 wt % in still another embodiment; and from about 10 wt % to about 90 wt % curing agent in yet another embodiment.

In preparing the curable resin formulation of the present invention, optional compounds may be added to the curable composition of the present invention including for example at least one cure catalyst to facilitate the reaction of the novel epoxy resin compound with the curing agent. The catalyst useful in the present invention may include for example, imidazole, acid catalysts, ammonium blocked acid catalysts, quaternary amines, superacid catalysts, metal complexes or any combination thereof.

Specific examples of catalysts suitable for use with the low viscosity epoxy compound of the present invention include imidazoles and other nitrogen heterocycles such as 1-methylimidazole, 2-methylimidazole, 2-phenylimidazole, 2,4-ethylmethylimidazole, DBU (1,8-diazabicyclo[5.4.0]undec-7-ene), DBN (1,5-diazabicyclo[4.3.0]non-5-ene), tertiary amines such as triethylamine, benzyldimethylamine, dimethylaminomethyl phenol, tris(dimethylaminomethyl) phenol, acid salts of these tertiary amines; phosphines such as triphenyl phosphine; and mixtures thereof. Additional suitable catalysts for curing the composition include tertiary amine, quaternary ammonium halide, Lewis acids such as boron trifluoride, and any combination thereof or the like. Boric acid and borate derivatives such as trimethyl borate can be used in conjunction with the above catalysts to provide latency or extended pot life to the composition of the present invention. Any combination of one or more of the above compounds can also be used to facilitate the reaction of the novel epoxy resin compound with the curing agent when a curing agent is used in the composition.

Generally, the amount of catalyst used in the present invention, may be for example, from 0.01 wt % to about 10 wt % in one embodiment, from about 0.1 wt % to about 10 wt % in another embodiment; and from about 0.5 wt % to about 5 wt % in still another embodiment.

In another embodiment, the curable composition of the present invention that can be UV cured can include (a) at least one novel liquid epoxide compound of the present invention, such as DVHPTO; and (b) a photoinitiator to provide a UV curable composition. For example, a typical cationic photoinitiator useful in the present invention may include a commercially available photoinitiator such as CPI6992 or CPI6976 available from Aceto Corp. CPI6992 and CPI6976 are comprised of a mixed triaryl sulfonium hexafluorophosphate salt solution in propylene carbonate. Other examples of the photoinitiator useful in the present invention may include iodonium salts.

Other examples of suitable initiators useful in the present invention include aryl diazonium salts [e.g., PP-33 available from Asahi Denka Kogyo K.K.], aryl iodonium salts, arylsulfonium salts [e.g., FC-509 available from Minnesota Mining and Manufacturing Company], UVE 1014 [available from G.E.], CP-66 and CP-77 [available from Asahi Denka Kogyo K. K.], SI-60L, SI-80L, SI-100L, and SI-110L [available from Sanshin Chemical Industry Co., Ltd.], and allene-ion complexes [e.g., CG-24-61 available from Ciba Geigy Ltd.]; and mixtures thereof.

Still in another embodiment, among the photoinitiators which may be used to achieve polymerization in the present invention are diazonium salts, diaryliodonium salts, triarylsulfonium salts, diaryliodosonium salts, triarylsulfoxonium salts, dialkylphenacylsulfonium salts, ferrocenium salts and dialkyl-4-hydroxyphenylsulfonium salts. Typically, these salts contain complex metal halide or other non-nucleophilic ions such as $BF_4-$, $PF_6-$, $SbF_6-$, $AsF_6-$, $ClO_4-$, $CF_3SO_3-$, and $(C_6F_5)_4B-$. Examples of suitable photoinitiator salts are described herein below and include those described in Crivello and Dietliker, Chemistry & Technology of UV & EB Formulation For Coatings, Inks & Paints, Vol. 3, 1991, page 329, the disclosure of which is hereby incorporated herein by reference.

The preferred photoinitiators useful in the present invention include diaryliodonium salts and phenacylsulfonium salts. Also preferred are sulfonium salts of the formula Ar—C(O)$CH_2$S+R'R"X— wherein Ar is monocyclic or bicyclic aryl or substituted aryl, such as phenyl, naphthyl, biphenyl, anthracenyl, phenanthryl, or heterocyclic such as furanyl or thiophenyl; R' and R" are the same or different and are alkyl, cycloalkyl or aromatic, and x- is a non-nucleophilic anion as described above.

Generally, the amount of photoinitiator used in the UV curable composition of the present invention may be for example, from 0.01 wt % to 10 wt % solids based on the weight of the epoxy compound or compounds in one embodiment, from 0.1 wt % to about 10 wt % solids in another embodiment, and from about 0.5 wt % to about 5 wt % solids in still another embodiment.

As noted herein, the compositions containing such epoxy compounds and one or more photoinitiators for polymerization of such compounds comprise one aspect of the present invention. Rapid and complete polymerization of the epoxy compounds can be achieved by irradiating the composition with an electron beam or x-ray dose on the order of 0.1 to 10 Mrad or ultraviolet radiation flux on the order of 10-30 mW/cm2. Higher energy levels are also useful, especially when higher throughput speeds are desired or thicker masses of polymer are presented.

Photopolymerizable compositions containing the epoxy compounds of the present invention can also contain any of the other additives customary for such uses, in the amounts thereof adequate to enable the additive to perform its desired function. Such additives include photosensitizers, fillers, and flow control agents. Examples of suitable materials for providing these functions abound in this field and are well known to those experienced in this field, and include the materials which are employed for those functions.

The novel compound of the present invention such as DVHPTO, which is the epoxy resin component of the curable composition of the present invention, may be used as the sole resin to form the epoxy matrix in the final curable formulation; or the novel compound such as DVHPTO may be used in combination with another second epoxy resin that is different from DVHPTO; and the combination may be used as the epoxy component in the final curable formulation.

In one embodiment for example, an epoxy resin (herein the second epoxy) which is different from the DVHPTO, may be optionally used in the curable composition of the present invention. The second epoxy may be any epoxy compound or combination of two or more epoxy compounds known in the art such as epoxy resins described in Lee, H. and Neville, K., *Handbook of Epoxy Resins*, McGraw-Hill Book Company, New York, 1967, Chapter 2, pages 2-1 to 2-27, incorporated herein by reference. In a preferred embodiment, the second epoxy compound may include for example epoxy resins based on reaction products of polyfunctional alcohols, phenols, cycloaliphatic carboxylic acids, aromatic amines, or aminophenols with epichlorohydrin. A few non-limiting embodiments include, for example, bisphenol A diglycidyl ether, bisphenol F diglycidyl ether, resorcinol diglycidyl ether, and triglycidyl ethers of para-aminophenols. Other suitable epoxy resins known in the art include for example reaction products of epichlorohydrin with o-cresol novolacs, hydrocarbon novolacs, and, phenol novolacs. The epoxy resin may also be selected from commercially available products such as for example, D.E.R. 331®, D.E.R. 332, D.E.R. 354, D.E.R. 580, D.E.N.® 425, D.E.N. 431, D.E.N. 438, D.E.R. 736, or D.E.R. 732 epoxy resins available from The Dow Chemical Company.

Generally, the amount of other epoxy resin, when used in the curable composition of the present invention, may be for example, from 0 wt % to about 99 wt % in one embodiment, from about 0.01 wt % to about 98 wt % in another embodiment; from about 1 wt % to about 95 wt % in still another embodiment; and from about 10 wt % to about 95 wt % in yet another embodiment, based on the total weight of the composition.

Other optional compounds that may be added to the curable composition of the present invention may include compounds that are normally used in resin formulations known to those skilled in the art. For example, the optional components may comprise compounds that can be added to the composition to enhance application properties (e.g. surface tension modifiers or flow aids), reliability properties (e.g. adhesion promoters) the reaction rate, the selectivity of the reaction, and/or the catalyst lifetime.

Other optional compounds that may be added to the curable composition of the present invention may include, for example, a solvent to lower the viscosity of the formulation further, other resins such as a phenolic resin that can be blended with the epoxy resin of the formulation, other epoxy resins different from the novel epoxy compound of the present invention (for example, aromatic and aliphatic glycidyl ethers; cycloaliphatic epoxy resins; and divinylarene dioxides such as divinylbenzene dioxide), other curing agents, fillers, pigments, toughening agents, flow modifiers, adhesion promoters, diluents, stabilizers, plasticizers, catalyst de-activators, flame retardants, and mixtures thereof. The optional compound(s) selected from the above described compounds to be added to the curable composition of the present invention can depend on the enduse in which the curable composition will be used.

For example, a solvent useful in the curable composition may include methyl isobutyl ketone, Dowanol® PM, cyclohexanone, toluene, methyl ethyl ketone or any combination thereof, to lower the viscosity of the formulation further than the inherent viscosity of the low viscosity epoxy compound, if desired.

In another embodiment, specific examples of fillers useful for adding to the curable composition of the present invention may include talc, clay, calcium carbonate, silica, alumina, sand, silicon carbide, boron nitride, boron carbide, aluminum nitride, and mixtures thereof. For electrical and/or thermal conductivity, fillers such as carbon, graphite, carbon fibers, silver, copper, and aluminum may also be used.

Generally, the amount of other optional components, when used in the present invention, may be for example, from 0 wt % to about 95 wt % in one embodiment, and from about 0.01 wt % to about 80 wt % in another embodiment.

The process for preparing the curable composition of the present invention includes admixing (a) at least one novel liquid epoxide compound of the present invention such as DVHPTO; (b) at least one curing agent such as an amine or a UV photoinitiator; and (c) optionally, at least one cure catalyst or other optional ingredients as needed. For example, the preparation of the curable resin formulation of the present invention is achieved by blending, in known mixing equipment, the novel compound, and the curing agent or a UV photoinitiator, and optionally any other desirable additives. Any of the above-mentioned optional additives, for example a curing catalyst, may be added to the composition during the mixing or prior to the mixing to form the composition.

All the components of the curable formulation are typically mixed and dispersed for example at room temperature (20-25° C.) or higher if necessary to enable the preparation of an effective curable epoxy resin composition having the desired balance of properties for a particular application.

The preparation of the curable formulation of the present invention, and/or any of the steps thereof, may be a batch or a continuous process. The mixing equipment used in the process may be any vessel and ancillary equipment well known to those skilled in the art.

The use of the novel liquid epoxide compound of the present invention, such as DVHPTO, can impart improved properties to the curable composition based on the improved properties of the monomer DVHPTO. For example, the curable formulation can exhibit a low volatility wherein the vapor pressure of the curable formulation may be similar to the vapor pressures of the monomer; or for example, the chloride content of the formulation can be less because the chloride content of the monomer DVHPTO is less.

Low volatility is important in many thermoset applications for several reasons. In order to maintain the correct epoxy/hardener ratio, which affects the final thermoset properties, the epoxy concentration must be constant. An epoxy with low volatility is important so evaporation is limited and a constant epoxy/hardener ratio can be maintained. Negative effects on the moisture uptake and glass transition temperatures may occur with a change in the epoxy/hardener stoichiometry also. Additionally, cure temperatures may be limited with a low volatility epoxy in order to prevent evaporation and void formation. Void formation can result in poor mechanical properties including decreased fracture toughness. The lower volatility of DVHPTO will eliminate this issue and prevent voids from forming during cure.

In addition, the Tg of the cured product made from the curable composition of the present invention is improved over conventional glycidyl ether, glycidyl ester or glycidyl amine epoxy resin formulations.

The unique combination of low viscosity of DVHPTO in the uncured state, and high Tg of the cured product prepared from DVHPTO, enables a formulator to apply new formulation strategies. In addition, the ability to cure the epoxy resin of the present invention with an expanded hardener range, offers the formulator significantly improved formulation latitude over other conventional types of epoxy resins such as cycloaliphatic epoxy resins.

In other embodiment, various novel epoxy compounds described with reference to Structure (I), advantageously can have one or more beneficial properties including for example low viscosity, absence of chlorine atoms, and low volatility; and when cured, the various novel epoxy compounds can impart a high glass transition temperature (Tg) to a thermoset. For example, in one specific embodiment, the epoxy compound a combination of all of the benefits described above, that is, the epoxy compound can have a viscosity of from about 0.3 Pa s to about 0.01 Pa s, a chlorine atom content of from less than about 500 ppm to less than about 100 ppm chlorine, a volatility (vapor pressure) of from about 0.001 mmHg to about 0.0000001 mmHg; and can impart to a thermoset a Tg of from about 50° C. to about 350° C.

The process of the present invention includes curing the curable resin composition to form a thermoset or cured composition. The process of curing the curable composition may be carried out at a predetermined temperature and for a predetermined period of time sufficient to cure the composition and the curing may be dependent on the hardeners used in the formulation. For example, the temperature of curing the formulation may be generally from about 10° C. to about 325° C. in one embodiment; from about 25° C. to about 300° C. in another embodiment; and from about 80° C. to about 250° C. in still another embodiment.

In general, the curing time of the curable composition may be chosen between about 1 minute to about 6 hours in one embodiment, between about 5 minutes to about 4 hours in another embodiment, and between about 10 minutes to about 2 hours in still another embodiment. Below a period of time of about 1 minute, the time may be too short to ensure sufficient reaction under conventional processing conditions; and above about 6 hours, the time may be too long to be practical or economical.

The cured product (i.e. the cross-linked product made from the curable composition) of the present invention shows several improved properties over conventional epoxy cured resins. For example, the cured product of the present invention may advantageously have a high Tg. For example, the cured product of the present invention, such as DVHPTO, may provide a thermoset, when cured, exhibiting a high Tg generally in the range of from about 50° C. to about 350° C. in one embodiment, and from about 80° C. to about 300° C. in another embodiment. The Tg of the cured product can be measured by differential scanning calorimetry or dynamic mechanical analysis.

The curable formulation or composition containing the DVHPTO compound of the present invention can be cured to form a thermoset, and in turn, such a thermoset may be useful in various applications where thermosets are conventionally used.

EXAMPLES

The following examples and comparative examples further illustrate the present invention in detail but are not to be construed to limit the scope thereof.

Various terms and designations used in the following examples are explained herein below:

"DVHPTO" stands for divinylhexahydropentalene trioxide also known as 2,4-di(oxiran-2-yl)octahydropentaleno[1,2-b]oxirene and as illustrated in Structure (I) above.

"DVHP" stands for divinyl hexahydro pentalene, also called 2,4-divinylbicyclo[3.3.0]oct-6-ene also called 1,3-divinyl-1,2,3,3a,4,6a-hexahydropentalene.

"TVCPTO" stands for trivinylcyclopentane trioxide also called 2,2',2''-(cyclopentane-1,2,4-triyl)tris(oxirane).

"TVCP" stands for trivinylcyclopentane also called 1,2,4-trivinylcyclopentane. TVCP was synthesized according to Designed Monomers and Polymers (2004), 7(6), pp 661-676.

"DVCPDO" stands for divinylcyclopentane dioxide also called 1,3-di(oxiran-2-yl)cyclopentane.

"DVCP" stands for divinylcyclopentane also called 1,3-divinylcyclopentane. DVCP was synthesized according to Designed Monomers and Polymers (2004), 7(6), pp 661-676.

"IPDA" stands for isophoronediamine.

"PACM" stands for 4,4'-methylenebis-cyclohexanamine.

"DVBDO" stands for divinyl benzene dioxide.

"mCPBA" stands for meta-chloroperoxy benzoic acid.

ECA100 refers to Epoxy Curing Agent 100. ECA100 is an anhydride hardener that is commercially available from Dixie Chemical Company, Inc.; and is composed of methyltetrahydrophthalic anhydride and tetrahydrophthalic anhydride.

EMI-24-CN is 1-(2-cyanoethyl)-2-ethyl-4(5)-methylimidazole and commercially available from PCI Synthesis.

"2-MI" stands for 2-methyl imidazole.

D.E.R. 354 is bisphenol F diglycidyl ether resin having an EEW of about 170; D.E.R 383 is bisphenol A diglycidyl ether resin having an EEW of about 180 g/equivalent; and D.E.R. 560 is a brominated epoxy resin; all products which are commercially available from The Dow Chemical Company.

UVI 6992 is a product containing approximately 55 wt % propylene carbonate and approximately 45 wt % mixed triaryl sulfonium salts; and is commercially available from Aceto Corp.

Xiameter® OFS-6040 is an epoxy-functionalized trimethoxy silane commercially available from Dow Corning.

Jeffamine® D230 is a difunctional polyetheramine commercially available from Huntsman.

MP8FS Silica is a silica particles product having a mean particle size of 0.7 µm; and MP15EF Silica is a silica particles product having a mean particle size of 1.1 µm; both products which are commercially available from Tatsumori.

Epodil® 749 is a reactive diluent which is the diglycidyl ether of neopentyl glycol; Epodil® 750 is the diglycidyl ether of 1,4-butanediol; and Epodil® 757 is the diglycidyl ether of cyclohexane dimethanol; all products of which are commercially available from Air Products.

EpiClon 830 LVP is high purity bisphenol F epoxy resin available from DIC Corp.

Kayahard AA is 4,4'-methylenebis-(2-ethylaniline) available from Nippon Kayaku.

SMA EF-40 is a styrene-maleic anhydride copolymer with a styrene:maleic anhydride ratio of approximately 4:1 and is commercially available from Cray Valley.

Byk®-W 996 and Byk A530 are both wetting and dispersing agent available from Byk Chemie.

MEK stands for methyl ethyl ketone and is available from Fisher Scientific.

The following standard analytical equipments and methods are used in the Examples to provide the results described in the Examples:

Gas Chromatography-Mass Spectrometry (GC-MS) traces were obtained using an Agilent Technologies 7890 A instrument. The GC conditions used were as follows:
Column: Agilent Technologies, Inc., catalog #19091S-951, 7.5 m, 0.25 m×1 µm
Split: 5:1
Injection volume: 0.1 µL
Carrier gas: hydrogen
Column flow: 3.5 mL/minute
Oven Temperature: 100° C. for (0 minute) then 25° C./minute until 300° C.; hold at 300° C. for 2 minutes
Detector: FID $^1$H and $^{13}$C-NMR spectra were recorded on a Bruker AV400 spectrometer and referenced to $CDCl_3$.

Attenuated Total Reflection Infrared Spectroscopy (ATIR) spectra were collected on a Nicolet Nexus 670 equipped with a horizontal attenuated total reflection accessory. The ATIR spectra were collected on the neat materials.

High resolution mass spectrometry samples were analyzed using a Waters Synapt G2 hybrid electrospray ionization quadrupole time-of-flight (TOF) mass spectrometer available from Waters Corporation. Mass spectra were obtained in the positive ion mode with the capillary (2500 V), cone (40 V), source temperature (110° C.), desolvation chamber (250° C.) and TOF mass analyzer potentials optimized to achieve the best signal-to-noise ratio. A curtain of nitrogen drying gas was utilized to assist in the electrospray ionization (ESI) process. All spectra were acquired in the reflectron "resolution" mode ("V" mode) of the TOF mass spectrometer (which has a mass range up to 4,000 g/mol), and had mass resolutions greater than 20,000 full width at half maximum; isotopic resolution was observed throughout the entire mass range detected. External mass calibration was performed using sodium formate and a fifteen-point calibration method. Internal mass calibration was subsequently performed using the peptide leu-enkephalin (Tyr-Gly-Gly-Phe-Leu) to yield monoisotopic masses exhibiting a mass accuracy better than Δm=±0.001 g/mol. The instrument was calibrated before every measurement to ensure constant experimental conditions.

Glass Transition Temperature

Glass transition temperature (Tg) was obtained via Dynamic Mechanical Thermal Analysis. For the analysis, a three-point bend test was used to collect tan delta data. Samples were approximately 12.5 mm wide and 12 mm long. The samples were then measured with a caliper, placed on the 10 mm 3-Point Bend Fixture of the TA Instruments RSA III Rheometer and tested in a closed oven with a constant nitrogen flow. A dynamic temperature ramp was performed: samples were measured with an oscillatory test (1 Hz) along a temperature ramp (5° C./minute) starting from room temperature and stopping at 300° C. Tg was reported as peak tan delta.

Viscosity

Viscosities were collected using an AR2000EX stress controlled rheometer (TA Instruments) with cone-and-plate geometry (stainless steel 40 mm, 2° cone, 51 micron truncation gap). A shear rate of 10 sec$^{-1}$ is used for these measurements. After equilibrating at 25° C. for 30 s, the temperature is ramped from 25° C. to 90° C. at a rate of 2° C./minute, with 10 points collected per decade. Temperature control is achieved with a Peltier plate and water bath circulator.

Glass Slide Test Vehicle to Collect Flow Time

A glass slide flow test vehicle as known in the art is constructed by placing 2 pieces of 50 µm thick tape onto opposite sides of a glass slide. A cover slip is placed on top of the tape to create a 50 µm gap and the cover slip is taped in place. Underfill is applied along one side of the cover slip and the time it takes to fill the area under the glass cover slip is recorded as the flow time.

Thermogravimetric Analysis (TGA)

To determine weight loss during cure, a 40 mg (+/−1 mg) sample was placed in a TGA pan and ramped to 150° C. at a rate of 10° C./minute and held isothermally at that temperature for 20 minutes.

Dynamic Scanning Calorimetry (DSC)

To obtain Tg for Example 8 and Comparative Examples H-K, a TA Instruments Q2000 DSC was used to measure glass transition temperatures ($T_g$). The uncured sample was placed in a DSC pan and then the $T_g$ was measured using the following method:
1: Ramp 10° C./minute to 250° C.,
2: Isothermal for 10 minutes,
3: Equilibrate at 25° C., and
4: Ramp 10° C./minute to 220° C.

The $T_g$ was found using the half-extrapolated tangents method on the data from the second thermal ramp.

Vapor Pressure

Vapor pressure data were measured using a GC method. A compound with a similar structure and known vapor pressure is analyzed as a reference with the unknown compounds. Divinylbenzene dioxide was used a reference compound in this method. Solutions of three epoxides and DVBDO were prepared at a concentration of 0.1 wt % in tetrahydrofuran (THF). Retention time data for the reference solution, sample solution, and methane were recorded while the GC oven was maintained isothermally.

The steps for calculating vapor pressure from the retention time are:

1. Calculate k' at all temperatures for the reference and unknown components.

$$k'_i = \frac{t_i - t_g}{t_g}$$

wherein $k_i'$=capacity factor for component i; $t_i$=retention time for component i (minutes); and $t_g$=retention time for methane (minutes).

2. Plot 1/RT vs. ln (k'/RT) for all components:
wherein R=gas constant; and T=temperature (K).
The slope of this plot is −ΔHs (heat of solution)

3. Plot ln P vs. ln (k'/RT) for the reference component and calculate the slope and y-intercept:
wherein P=vapor pressure; M=slope of the plot; and N=intercept of the plot.

The slope of this plot is ΔHs/ΔHv. Assuming an 'Enthalpy Rule', the slope and intercept of this plot for similar compounds will be constant.

4. Calculate vapor pressure of unknown components at experimental temperatures by solving equation for P.

$$M \ln P_i = \ln\left(\frac{k_i'}{RT}\right) - N$$

wherein Pi=vapor pressure of component i at temperature T.

This calculation is repeated for all components at all temperatures. The retention time for methane was used to determine the dead time for the GC column The GC conditions for this method are summarized in Table A.

TABLE A

| Gas Chromatograph Conditions for Vapor Pressure Measurements | |
|---|---|
| Chromatograph: | Agilent 6890 (GC66) |
| Column: | RX1 ®-1MS 15 m × 0.25 mm × 1 μm SN 962675 |
| Detector: | FID |
| Temperatures: | |
| Oven: | Isothermal at the temperature of interest (130-230° C.) for 15 min; 300° C., hold 1 min. |
| Injector: | 300° C. |
| Detector: | 280° C. |
| Flows: | |
| Carrier: | 12 psi Helium (1.7 mL/min) |
| Split: | 80:1 |
| Make-Up: | 25 mL/min Helium |
| Air: | 350 mL/min |
| Hydrogen: | 30 mL/min |
| Sample Size: | 1.0 μL |
| Data System: | Thermo Atlas |

Example 1

Part A. Preparation of DVHP Intermediate (Method 1)

A 600 mL Parr reactor was charged with 300 mL of toluene and 64 mg (0.08 mmol) of the following ruthenium catalyst:

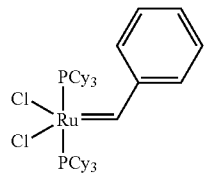

The reactor was purged 3 times with ethylene to a pressure of 1,482 kPa (215 psi) and the resulting mixture was stirred for 20 minutes. The pressure in the reactor was safely released and 10.7 g (81 mmol) of dicyclopentadiene (DCPD) dissolved in toluene (20 mL) was added to the mixture. The pressure in the reactor was increased to 1,482 kPa (215 psi) and the resulting mixture was stirred for 24 hours. A 1 mL aliquot of the reaction mixture was removed and analyzed by GC-MS. The analysis showed that the reaction was complete. The mixture was removed from the reactor and treated with 15% $H_2O_2$ (100 mL) for 10 minutes. The organic layer formed in the reactor was isolated, washed with water (100 mL), dried over $MgSO_4$, and filtered through a plug of silica. To the filtrate t-butylcatechol (10 mg) was added and the solvent was removed under reduced pressure (0.013 kPa, 0.1 mmHg) to afford a nearly colorless liquid (Mass=10.8 g; 83% yield, which was identified as DVHP).

Part A. Preparation of DVHP Intermediate (Method 2)

A 600 mL Parr reactor was charged with 300 mL of toluene and 64 mg (0.08 mmol) of the following ruthenium catalyst:

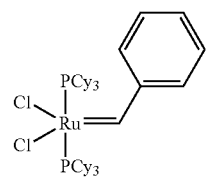

The reactor was purged 3 times with ethylene to a pressure of 1,482 kPa (215 psi) and the resulting mixture was stirred for 20 minutes. The pressure in the reactor was safely released and 10.7 g (81 mmol) of dicyclopentadiene (DCPD) dissolved in toluene (20 mL) was added to the mixture. The reactor pressure was increased to 1,482 kPa (215 psi) with ethylene and the resulting mixture was stirred for 24 hours. The ethylene was vented from the reactor and 2-mercaptonicotinic acid (0.4 mmol), dissolved in acetonitrile (20 mL) was added. The mixture was stirred for 2 hours and t-butylcatechol (10 mg) was added. The mixture was removed from the Parr reactor and the solvent was removed under reduced pressure to afford crude DVHP. The mixture was distilled (0.013 kPa, 0.1 mmHg) to afford a nearly colorless liquid (Mass=11.5 g; 88% yield, which was identified as DVHP).

The process of preparing DVHP can be illustrated by the following reaction scheme:

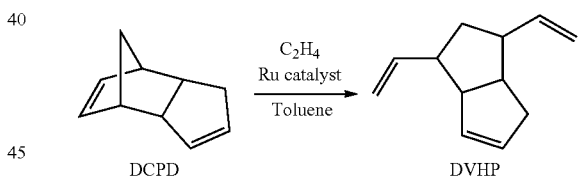

Characterization Data for DVHP

The data used for characterizing DVHP was generated by NMR spectroscopy and high resolution mass spectrometry and the results are as follows:

$^1$H NMR (400 MHz, $CDCl_3$) δ 5.84 (m, 2H), 5.70 (m, 1H), 5.51 (dd, J=5.7, 2.4 Hz, 1H), 5.01 (m, 4H), 3.29 (ddd, J=8.7, 6.3, 2.3 Hz, 1H), 2.87 (m, 1H), 2.66 (m, 2H), 2.28 (ddd, J=7.9, 4.2, 2.0 Hz, 2H), 1.63 (m, 1H), 1.33 (q, J=12.2 Hz, 1H).

$^{13}$C NMR (101 MHz, $CDCl_3$) δ 140.48, 140.15, 131.84, 130.50, 114.57, 113.93, 54.90, 48.13, 47.06, 43.99, 34.97, 34.43.

Part B. Preparation of DVHPTO Product (Structure II) (Method 1)

To a 2 L round bottomed flask equipped with a thermometer, pH meter, and mechanical stirrer was added DVHP (19.66 g, 0.123 mol, 1 equiv.), acetone (500 mL), and an aqueous solution of sodium bicarbonate (54.82 g dissolved in 200 mL of water). Oxone® solution (161.6 g, 0.468 mol, 3.8 equiv) was added slowly to the DVHP mixture over 45 minutes to maintain a reaction temperature of approximately 25° C. and pH between 7-8. A water bath was used to keep the reaction at room temperature (about 25° C.), while the addition of aqueous KOH was used to moderate the pH. The reaction was allowed to stir at room temperature for an additional 3½ hours, after which the solid by-product was removed via filtration and washed with $CH_2Cl_2$. The filtrate was phase separated and the aqueous phase was extracted with $CH_2Cl_2$. The organic extracts were combined. The extracts were then washed, first with saturated $NaHCO_3$ (150 mL) and then with water (150 mL). The resultant organic phase was dried over $Na_2SO_4$, and filtered. DVHPTO was isolated as a clear liquid in 70% yield upon removing the solvent on a rotary evaporator.

Characterization of DVHPTO Product

The data used for characterizing DVHPTO was generated by NMR spectroscopy and high resolution mass spectrometry (HRMS) and the results are as follows:

$^1$H NMR (400 MHz, CDCl3) δ 3.46 (m, 2H), 2.70 (m, 5H), 2.33 (m, 3H), 2.00 (m, 2H), 1.64 (m, 2H), 1.49 (m, 1H), 1.23 (dd, J=24.6, 12.3 Hz, 1H).

$^{13}$C NMR (101 MHz, $CDCl_3$) δ 59.34, 59.18, 58.89, 58.73, 58.33, 58.23, 58.00, 57.87, 52.85, 52.77, 51.82, 51.74, 51.68, 51.62, 47.25, 47.21, 47.01, 46.97, 46.90, 46.87, 46.41, 46.35, 45.34, 45.01, 44.88, 44.04, 43.75, 43.30, 43.22, 42.76, 42.54, 42.15, 41.96, 41.94, 41.82, 40.33, 40.21, 29.12, 28.60, 28.58, 28.41, 28.37, 28.20, 27.72, 27.29.

HRMS (ESI) calculated for $C_{12}H_{16}O_3$ [M+Na] 231.10997, found 231.10997.

Preparation of DVHPTO Product (Structure II) (Method 2)

DVHP (2 g, 0.012 mol, 1 equiv) and $CH_2Cl_2$ (20 mL) were added to a 100 mL 2-necked round bottom flask. The solution was cooled to 0° C. in an ice water bath. Then, mCPBA (10.07 g, 0.045 mol, 3.6 equiv) was added over 15 minutes at 0° C., after which the reaction was allowed to warm to room temperature. A white precipitate formed and a slight exotherm was observed.

After 1.5 hours, the reaction was filtered and the filtrate was washed with saturated $K_2CO_3$ (3×10 mL), brine (1×10 mL) and then with water (1×10 mL). The organic layer was dried over $MgSO_4$, filtered, and concentrated on a rotovap to yield 1.18 g of DVHPTO (45% yield). The resultant product was characterized by GC/MS and contained mostly DVHPTO. The resultant product also contained a small amount of benzoic acid and the diepoxide of DVHP (DVHPDO).

Example 2

Preparation of Trivinyl Cyclopentane Triepoxide (TVCPTO) (Structure IV)

To a 200 mL round bottomed flask equipped with a thermometer, pH meter, and mechanical stirrer was added trivinylcyclopentane (2 g, 0.013 mol, 1 equiv.), acetone (75 mL), and an aqueous solution of sodium bicarbonate (10.11 g, 0.121 mol dissolved in 75 mL of water). Oxone® solution (23.30 g, 0.067 mol, 5 equiv) was added slowly to the DVHP mixture over 20 minutes to maintain a reaction temperature of approximately 25° C. and pH between 7-8. A water bath was used to keep the reaction at room temperature, while the addition of aqueous KOH was used to moderate the pH. The reaction was allowed to stir at room temperature for an additional 3½ hours, after which the resulting reaction mixture was filtered. The solid by-product was washed with $CH_2Cl_2$. The filtrate was phase separated and the aqueous phase was extracted with $CH_2Cl_2$. The organic phases were combined and washed, first with saturated $NaHCO_3$ (1×30 mL) and then with water (1×30 mL). The organic phase was dried over $Na_2SO_4$, and filtered. Trivinyl cyclopentane triepoxide was isolated as a clear liquid in 70% yield upon removing the solvent on a rotary evaporator.

Characterization of Trivinyl Cyclopentane Triepoxide Product (TVCPTO)

HRMS (ESI) calculated for $C_{12}H_{16}O_3$ [M+Na] 219.0992, found 219.1000.

$^1$H NMR (400 MHz, $CDCl_3$) δ 3.07-2.94 (m, 0.5H), 2.93-2.82 (m, 0.5H), 2.72 (dd, J=3.5, 2.4 Hz, 1H), 2.67-2.50 (m, 3H), 2.42-2.23 (m, 3H), 1.87-1.71 (m, 6H), 1.41-1.08 (m, 2H).

$^{13}$C NMR (101 MHz, $CDCl_3$) δ 54.76, 54.61, 54.43, 54.38, 54.34, 54.27, 54.19, 54.04, 54.01, 53.96, 53.90, 53.86, 53.53, 53.44, 53.05, 52.77, 52.63, 52.59, 52.38, 52.34, 52.27, 52.17, 52.11, 50.03, 48.44, 46.98, 46.53, 46.44, 46.26, 46.13, 46.05, 46.00, 45.92, 45.86, 45.42, 45.34, 45.24, 44.97, 44.87, 44.76, 44.50, 44.39, 44.27, 44.24, 44.18, 44.12, 43.95, 43.82, 43.56, 43.31, 43.22, 43.18, 43.09, 42.89, 41.36, 40.79, 40.65, 40.57, 40.06, 39.81, 39.72, 39.65, 39.26, 38.18, 37.58, 35.54, 31.91, 31.68, 31.53, 31.38, 31.29, 31.20, 30.98, 30.88, 30.81, 30.76, 30.66, 30.58, 30.46, 30.32, 29.63, 29.38, 28.90, 28.74, 28.10, 27.36.

Example 3-5 and Comparative Examples A-F

Several thermosets were prepared with various concentrations of the components described in Table I as follows: The compounds in each of the examples described in Table I were thoroughly mixed together to form a resin mixture. Each one of the resin mixtures of Table I were separately coated onto a 10 cm by 10 cm piece of interwoven glass cloth. Then the resultant coated cloth was cured in an oven at 100° C. for 1 hour, followed by a post-cure at 220° C. for 2 hours.

TABLE I

| EXAMPLE | COMPONENTS | | | | | | |
|---|---|---|---|---|---|---|---|
| | DVHPTO (g) | IPDA (g) | PACM (g) | ECA100 (g) | DVBDO (g) | D.E.R. 354 (g) | EMI-24-CN (g) |
| Example 3 | 0.63 | 0.37 | | | | | |
| Example 4 | 2.33 | | 1.67 | | | | |
| Example 5 | 0.40 | | | 0.59 | | | 0.01 |
| Comparative Example A | | 10.00 | | | 5.00 | | |
| Comparative Example B | | | 2.67 | | 4.33 | | |

TABLE I-continued

| EXAMPLE | DVHPTO (g) | IPDA (g) | PACM (g) | ECA100 (g) | DVBDO (g) | D.E.R. 354 (g) | EMI-24-CN (g) |
|---|---|---|---|---|---|---|---|
| Comparative Example C | | | | 3.28 | 4.64 | | 0.08 |
| Comparative Example D | 1.43 | | | | | 6.09 | |
| Comparative Example E | | 1.67 | | | | 5.84 | |
| Comparative Example F | | | | 1.46 | | 4.48 | 0.06 |

The glass transition temperature for the cured formulations in Examples 3-5 and Comparative Examples A-F were collected using the dynamic mechanical analysis method described above. The data are illustrated in Table II below.

TABLE II

| | EPOXY | | |
|---|---|---|---|
| HARDENER | Examples 3-5 DVHPTO Tg (° C.) | Comparative Examples A-C DVBDO Tg (° C.) | Comparative Examples D-F D.E.R. 354 Tg (° C.) |
| IPDA | 223 | 227 | 118 |
| PACM | 261 | 228 | 122 |
| ECA100 | 250 | 115 | 111 |

Examples 6 and 7

Thermosets for UV Coatings

DVHPTO and UVI 6992 catalyst were combined in accordance with the weights shown in Table III; and then the mixture was applied to Bonderite steel panels as a film having a thickness of 12 microns. The panels were UV processed using a 240 W/cm mercury bulb to form a coating. The formulations cured to give coated panels.

TABLE III

| Compound | Example 6 (g) | Example 7 (g) |
|---|---|---|
| DVHPTO | 10.05 | 8.29 |
| UVI 6992 Catalyst | 0.057 | 0.17 |

Example 8

Thermoset for Underfill Adhesive

DVHPTO, silica, and carbon black were added to a polyethylene FlackTek™ speed mixing container and mixed using a FlackTek™ DAC150 speed mixer for 30 seconds (s) at 2500 revolutions per minute (rpm). Xiameter® OFS-6040 silane (1.1 wt % on silica) was added to the FlackTek™ DAC150 speed mixer; and the resulting sample was mixed for 30 s at 2500 rpm. Jeffamine® D230 was added to the sample and then the sample was further mixed for 30 s at 2500 rpm. The sample was roll-milled using a 3 roll mill. The weight of IPDA was re-calculated to account for material losses during roll milling and then the IPDA was added to the sample. The sample was mixed again at 2500 rpm for 30 s and then degassed for 15 minutes under vacuum in a bell jar. The weight percent of each component is described in Table IV.

TABLE IV

| Component | Weight % of Component |
|---|---|
| IPDA | 3.27 |
| DVHPTO | 26.15 |
| Jeffamine ® D230 | 9.81 |
| MP8FS Silica | 60.00 |
| Xiameter ® OFS- 6040 silane | 0.66 |
| Carbon black | 0.12 |

Comparative Example G

EpiClon EXA 830-LVP and silica were added to a polyethylene FlackTek™ speed mixing container and mixed using a FlackTek™ DAC150 speed mixer for 30 s at 2500 rpm. Xiameter® OFS-6040 silane (1.1 wt % on silica) was added and the sample was mixed for 30 s at 2500 rpm. Byk®-W 996 was added and the sample mixed for 30 s at 2500 rpm. Byk® A530 was added and the sample mixed for 30 s at 2500 rpm. Kayahard AA was then added and the sample mixed for 30× at 2500 rpm. The sample was then degassed for 15 minutes under vacuum in a bell jar. The weight percent of each component is listed in Table V.

TABLE V

| Component | Weight % Component |
|---|---|
| EpiClon 830LVP | 36.46 |
| Kayahard AA | 12.54 |
| MP15EF | 50.00 |
| Xiameter ® OFS- 6040 silane | 0.55 |
| Byk W-996 | 0.20 |
| Byk A530 | 0.25 |

The properties of the underfill from Example 8 were measured and are shown in Table VI. The viscosity of the underfill from Example 8 is lower relative to the control formulation and the flow time is faster.

TABLE VI

| Property | Comparative Example G | Example 8 |
|---|---|---|
| Viscosity (Pa-s) at 25° C. | 8.01 | 1.45 |
| Viscosity (Pa-s) at 85° C. | 0.10 | 0.09 |
| Tg After Cure (° C.) | 91 | 115 |
| Flow Time (s) | 72 | 33 |

Example 9

Reactive Diluent for Electronics

DVHPTO was added to D.E.R. 383 at various weight percents as described in Table VII. DVHPTO was shown to decrease the viscosity of the epoxy resin D.E.R. 383 as shown in Table VII.

TABLE VII

| | % DVHPTO in D.E.R. 383 | | | | | | |
|---|---|---|---|---|---|---|---|
| | 0 | 5 | 10 | 15 | 20 | 30 | 40 |
| Viscosity (Pa-s) | 9.2 | 7.2 | 5.8 | 4.8 | 3.9 | 2.6 | 1.6 |

Example 10

Reactive Diluent for Electronics

A formulation to investigate epoxy homopolymerization of D.E.R 383 with 1-methylimidazole as a catalyst and DVHPTO as a reactive diluent was prepared. The reagents in Table VIII were added to a polyethylene FlackTek™ speed mixing container and mixed for 30 s at 2500 rpm to prepare a homogeneous solution.

TABLE VIII

| Component | Example 10 |
|---|---|
| D.E.R. 383 | 81.6 |
| DVHPTO | 14.4 |
| 1-methylimidazole | 4.0 |

Comparative Examples H-K

Comparative formulations were prepared to investigate epoxy homopolymerization of D.E.R 383 with 1-methylimidazole as a catalyst and other reactive diluents. D.E.R. 383 (8.16 g), the diluent in Table IX (1.4 g) and 1-methylimidazole (0.4 g) were added to a polyethylene FlackTek™ speed mixing container and mixed for 30 s at 2500 rpm to prepare a homogeneous solution.

TABLE IX

| Example | Diluent |
|---|---|
| Example H | Control, no diluents included |
| Example I | Epodil ® 757 (CHDM-DGE) |
| Example J | Epodil ® 750 (BD-DGE) |
| Example K | Epodil ® 749 (NPG-DGE) |

The samples were analyzed for viscosity, Tg, and weight loss and the resulting data is described in Table X. DVHPTO decreases the viscosity of the resin and increases Tg.

TABLE X

| Resin Type | Viscosity @ 25° C. (Pa-s) | $T_g$ (° C.) | Weight Loss During Cure (%) |
|---|---|---|---|
| Control - no diluents (Comparative Example H) | 9.2 | 145 | 1.2 |
| DVHPTO (Example 9) | 4.8 | 164 | 2.7 |
| Epodil ® 757 (CHDM-DGE) (Comparative Example I) | 2.5 | 125 | 2.4 |
| Epodil ® 750 (BD-DGE) (Comparative Example J) | 1.2 | 118 | 3.1 |
| Epodil ® 749 (NPG-DGE) (Comparative Example K) | 1.7 | 118 | 4.3 |

Example 11

Electrical Laminate

D.E.R. 560 (60% in MEK), SMA-EF-40 (60% in MEK), DVHPTO, and 2-MI (20% in Dowanol PM) were weighed into a 200 mL jar and placed on a shaker until a homogeneous mixture was obtained. The weights used for the formulation are shown in Table XI. An epoxy/hardener ratio of 1.0 was used.

TABLE XI

| Reagents | EEW | Solids Weight | Solution Weights (g) |
|---|---|---|---|
| DER 560 (60% in MEK) | 455 | 31.2 | 52.0 |
| SMA EF-40 (60% in MEK) | 513 | 63.3 | 105.5 |
| DVHPTO | 104 | 5.7 | 5.7 |
| 2-MI (20% in Dowanol PM) | | 0.6 | 0.6 |

Comparative Example L

D.E.R. 560 (60% in MEK), SMA-EF-40 (60% in MEK), and 2-MI (20% in Dowanol PM) were weighed into a 200 mL jar and placed on a shaker until a homogeneous mixture was obtained. The weights used for the formulation are shown in Table XII.

TABLE XII

| Reagents | EEW | Solids Weight (g) | Solution Weights (g) |
|---|---|---|---|
| DER 560 (60% in MEK) | 455 | 47.0 | 78.3 |
| SMA EF-40 (60% in MEK) | 513 | 53.0 | 88.3 |
| 2-MI (20% in Dowanol PM) | | 0.6 | 0.6 |

The above formulations from Example 11 and Comparative Example L were gelled at 171° C. on a hot plate. The gelled samples were then post-cured for 2 hours at 200° C. in an oven. The cured samples were analyzed for Tg and the resulting data is shown in Table XIII. DVHPTO was shown to increase Tg.

TABLE XIII

| Resin Type | $T_g$ (° C.) |
|---|---|
| Example 11 with DVHPTO | 168 |
| Comparative Example L | 158 |

Comparative Example M

Preparation of Divinyl Cyclopentane Diepoxide (DVCPDO)

To a 100 mL round bottomed flask equipped with a thermometer, pH meter, and mechanical stirrer was added divinylcyclopentane (0.5 g, 0.0041 mol, 1 equiv.), acetone (25 mL), and an aqueous solution of sodium bicarbonate (3.07 g, 0.037 mol dissolved in 25 mL of water). Oxone® solution (4.24 g, 0.012 mol, 3 equiv) was added slowly to the DVCP mixture over 15 minutes to maintain a reaction temperature of approximately 25° C. and pH between 7-8. A water bath was used to keep the reaction at room temperature, while the addition of aqueous KOH was used to moderate the pH. The reaction was allowed to stir at room temperature for an additional 3½ hours, after which the resulting reaction mixture was filtered. The solid by-product was washed with $CH_2Cl_2$. The filtrate was phase separated and the aqueous phase was extracted with $CH_2Cl_2$. The organic phases were combined and washed, first with saturated $NaHCO_3$ (1×15 mL) and then with water (1×15 mL). The organic phase was dried over $Na_2SO_4$, and filtered. Divinyl cyclopentane diepoxide was isolated as a clear liquid upon removing the solvent on a rotary evaporator.

Characterization of Divinyl Cyclopentane Diepoxide Product (DVCPDO)

$^1$H NMR (400 MHz, $CDCl_3$) δ 2.52 (m,2H), 2.35 (m, 2H), 2.13 (m, 2H), 1.6-1.09 (m, 6H).

$^{13}$C NMR (101 MHz, $CDCl_3$) δ 54.79, 54.76, 54.69, 54.06, 50.84, 45.78, 45.70, 45.63, 45.47, 42.12, 41.82, 41.75, 36.98, 31.97, 31.92, 31.67, 28.2 7, 28.16, 28.14, 28.00, 26.48, 25.31.

Example 12 and 1 and Comparative Example N

Vapor Pressure Data

As shown in Table XIV below, the vapor pressure of TVCPTO and DVHPTO are lower relative to the comparative example divinyl cyclopentane diepoxide (DVCPDO). The decreased volatility is advantageous for reducing weight loss during cure and maintaining sample integrity.

TABLE XIV

| T (° C.) | DVCPDO Comparative Example N Comparative Example Vapor Pressure (mmHg) | TVCPTO Example 12 Structure IV Vapor Pressure (mmHg)[b] | DVHPTO Example 13 Structure II Vapor Pressure (mmHg)[b] |
|---|---|---|---|
| 130 | 8.48 | 0.60 | 0.22 |
| 140 | 14.63 | 1.20 | 0.45 |
| 150 | 23.91 | 2.26 | 0.89 |
| 160 | 37.57 | 4.10 | 1.67 |
| 170 | 57.52 | 7.17 | 3.03 |
| 180 | 84.32 | 12.09 | 5.32 |
| 190 | 115.44 | 19.32 | 8.79 |
| 200 | 162.79 | 30.38 | 14.40 |
| 210 | 214.92 | 46.43 | 23.18 |
| 220 | 269.10 | 67.01 | 33.45 |
| 230 | 346.15 | 94.66 | 50.09 |
| 25[a] | 4.81E-03 | 1.69E-05 | 2.58E-06 |
| 100[a] | 1.891 | 0.070 | 0.021 |

[a]Data was extrapolated to give vapor pressure at 25° C. and 100° C.
[b]Composite vapor pressure of all isomers.

What is claimed is:

1. A composition of matter comprising an epoxide compound having the following chemical structure:

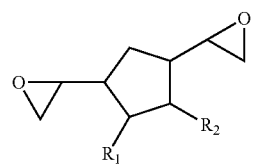

wherein $R_1$ and $R_2$ are bonded together to form a cycloalkane group having from 1 to 20 carbon atoms, wherein the cycloalkane group is optionally substituted with an oxirane group, or one of $R_1$ and $R_2$ is H, while the other is

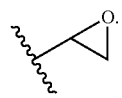

2. The composition of claim 1, wherein the epoxide compound has the following formula:

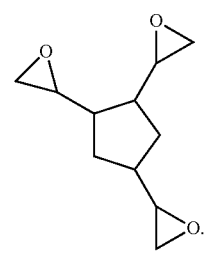 [SMILES: C1OC1C1CC(C2CO2)C(C2CO2)C1]

3. The composition of claim 1, wherein $R_1$ and $R_2$ are bonded together to form a cycloalkane with a bridging group having from 1 to 8 carbon atoms.

4. The composition of claim 1, wherein $R_1$ and $R_2$ are bonded together to form a cycloalkane group having from 1 to 20 carbon atoms, and wherein an oxirane group is attached to the cycloalkane group.

5. The composition of claim 1, wherein $R_1$ and $R_2$ bond together to form a cycloalkane with a bridging group having from 1 to 8 carbon atoms; and wherein the cycloalkane with a bridging group is substituted with an oxirane group.

6. The composition of claim 1, wherein the epoxide compound has the following chemical structure:

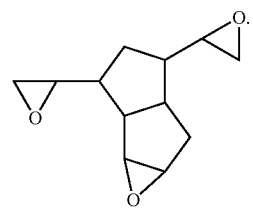 [SMILES: C1OC1C1CC(C2CO2)C2C1CC1OC12]

7. The composition of claim 1, wherein the epoxide compound has the following chemical structure:

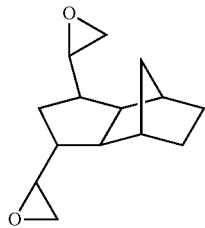

8. The composition of claim 1, wherein the epoxide compound has a viscosity of less than about 1 Pa-s.

9. A process for preparing a compound having the following chemical structure:

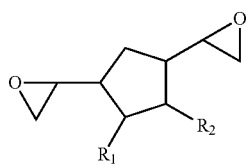

wherein $R_1$ and $R_2$ are bonded together to form a cycloalkane group having from 1 to 20 carbon atoms or wherein $R_1$ and $R_2$ are both a hydrocarbon group having from 1 to 20 carbon atoms, and wherein the $R_1$ and/or the $R_2$ group are substituted with an oxirane group, the process comprising the steps of:
(a) ring-opening metathesis of a cyclic olefin, and
(b) epoxidizing the product of step (a) to form the compound of the above chemical structure.

10. The process of claim 9, wherein the cyclic olefin consists of divinyl hexahydro pentalene.

11. The process of claim 9, wherein the epoxidation of step (b) is carried out by reacting the product of step (a) with at least one oxidizing agent.

12. The process of claim 9, wherein the at least one oxidizing agent comprises a percarboxylic acid.

13. The process of claim 12, wherein the percarboxylic acid is selected from the group consisting of peracetic acid, meta-chloroperoxybenzoic acid, and mixtures thereof.

14. The process of claim 9, wherein the epoxidation of step (b) is carried out by reacting the product of step (a) with a peroxomonosulfate and acetone.

15. The process of claim 9, wherein the epoxidation of step (b) is carried out by reacting the product of step (a) with hydrogen peroxide and a non-metal catalyst.

16. The process of claim 15, wherein the non-metal catalyst comprises acetonitrile to form a peroxyimidic acid that acts as the epoxidizing agent.

17. The process of claim 9, wherein the epoxidation of step (b) is carried out by reacting the product of step (a) with alkylhydroperoxides and a transition metal catalyst.

18. The process of claim 17, wherein the transition metal catalyst comprises a titanium catalyst, a chiral tartrate diester, tert-butylhydroperoxide, or mixtures thereof.

19. The process of claim 9, wherein the epoxidation of step (b) is carried out by reacting the product of step (a) with hydrogen peroxide and a metal catalyst.

20. The process of claim 9, wherein the metal catalyst comprises an Fe(III) complex of pyridine 2,6-dicarboxylic acid, Mn(III) complexes of 8-hydroxyquinoline and halogen substituted analogs, Mn(III) salen complexes, methyltrioxo rhenium, or mixtures thereof.

21. The process of claim 9, wherein the epoxidation of step (b) is carried out by reacting the product of step (a) with a heteropoly acid salt and phase transfer ammonium cations, zeolites, hydrotalcites, metal oxides, or mixtures thereof.

* * * * *